US007960599B2

(12) United States Patent  
Millis et al.

(10) Patent No.: US 7,960,599 B2  
(45) Date of Patent: Jun. 14, 2011

(54) METHOD FOR MAKING INDUSTRIAL CHEMICALS

(75) Inventors: James R. Millis, Plymouth, MN (US); Michael J. Tupy, Crystal, MN (US); Timothy W. Abraham, Minnetonka, MN (US); Mervyn L. De Souza, Plymouth, MN (US)

(73) Assignee: Elevance Renewable Sciences, Inc., Bolingbrook, IL (US)

( * ) Notice: Subject to any disclaimer, the term of this patent is extended or adjusted under 35 U.S.C. 154(b) by 857 days.

(21) Appl. No.: 10/542,167

(22) PCT Filed: Jan. 13, 2004

(86) PCT No.: PCT/US2004/000841  
§ 371 (c)(1),  
(2), (4) Date: May 4, 2007

(87) PCT Pub. No.: WO2004/062763  
PCT Pub. Date: Jul. 29, 2004

(65) Prior Publication Data  
US 2007/0270621 A1  Nov. 22, 2007

Related U.S. Application Data

(60) Provisional application No. 60/439,959, filed on Jan. 13, 2003.

(51) Int. Cl.  
*C07C 5/22* (2006.01)

(52) U.S. Cl. ........ 585/253; 585/242; 585/250; 585/264; 585/315; 585/324; 585/646; 585/647; 585/664; 585/804

(58) Field of Classification Search .................. 585/242, 585/250, 253, 264, 315, 324, 646, 647, 664, 585/804  
See application file for complete search history.

(56) References Cited

U.S. PATENT DOCUMENTS

| 2,174,247 | A | 9/1939 | McAllister |
| 4,435,606 | A | 3/1984 | Motz et al. |
| 4,943,396 | A | 7/1990 | Johnston |
| 5,312,940 | A | 5/1994 | Grubbs et al. |
| 5,710,298 | A | 1/1998 | Grubbs et al. |

(Continued)

FOREIGN PATENT DOCUMENTS

DE  282594 A1  3/1915

(Continued)

OTHER PUBLICATIONS

Jay J. Thelen and John B. Ohirogge (Metabolic Engineering Of Fatty Acid Biosy6nthesis In Plants; Metabolic Engineering 4, pp. 12-21 (2002) Elsevier Science.

(Continued)

*Primary Examiner* — Prem C Singh  
(74) *Attorney, Agent, or Firm* — Brinks Hofer Gilson & Lione

(57) ABSTRACT

A process for producing industrially important chemicals from renewable resources is disclosed. This "biobased" process employs readily available, renewable resources comprising fatty acids rather than exploiting fossil sources, such as coal and petroleum. In one embodiment of the process 1-octene, along with methyl-9-decenoate and butadiene, is produced from linoleic acid via an enzymemediated isomerization reaction, followed by a metathesis reaction with ethylene. Linoleic acid can be isolated from vegetable oils, such as soybean oil.

21 Claims, 2 Drawing Sheets

Conversion to 9-methyldecenoate from ethenolysis of conjugated methyl linoleate

U.S. PATENT DOCUMENTS

| | | | |
|---|---|---|---|
| 5,728,785 A | 3/1998 | Grubbs et al. |
| 5,728,917 A | 3/1998 | Grubbs et al. |
| 5,750,815 A | 5/1998 | Grubbs et al. |
| 5,811,515 A | 9/1998 | Grubbs et al. |
| 5,831,108 A | 11/1998 | Grubbs et al. |
| 5,849,851 A | 12/1998 | Grubbs et al. |
| 5,880,231 A | 3/1999 | Grubbs et al. |
| 5,917,071 A | 6/1999 | Grubbs et al. |
| 5,922,863 A | 7/1999 | Grubbs et al. |
| 5,939,504 A | 8/1999 | Woodson, Jr. et al. |
| 5,969,170 A | 10/1999 | Grubbs et al. |
| 5,977,393 A | 11/1999 | Grubbs et al. |
| 6,020,443 A | 2/2000 | Woodson, Jr. et al. |
| 6,040,363 A | 3/2000 | Warner et al. |
| 6,060,304 A | 5/2000 | Pariza et al. |
| 6,080,826 A | 6/2000 | Grubbs et al. |
| 6,107,420 A | 8/2000 | Grubbs et al. |
| 6,197,894 B1 | 3/2001 | Sunaga et al. |
| 6,211,315 B1 | 4/2001 | Larock et al. |
| 6,215,019 B1 | 4/2001 | Pederson et al. |
| 6,284,852 B1 | 9/2001 | Lynn et al. |
| 6,306,988 B1 | 10/2001 | Grubbs et al. |
| 6,310,121 B1 | 10/2001 | Woodson, Jr et al. |
| 6,316,380 B1 | 11/2001 | Nolan et al. |
| 6,316,645 B1 | 11/2001 | Sih et al. |
| 6,323,296 B1 | 11/2001 | Warner et al. |
| 6,376,690 B1 | 4/2002 | Grubbs et al. |
| 6,409,875 B1 | 6/2002 | Giardello et al. |
| 6,410,110 B1 | 6/2002 | Warner et al. |
| 6,410,666 B1 | 6/2002 | Grubbs et al. |
| 6,426,419 B1 | 7/2002 | Grubbs et al. |
| 6,433,101 B1 | 8/2002 | Woodson et al. |
| 6,465,590 B1 | 10/2002 | Maughon et al. |
| 6,525,125 B1 | 2/2003 | Giardello et al. |
| 6,583,236 B1 | 6/2003 | Giardello et al. |
| 6,610,626 B2 | 8/2003 | Grubbs et al. |
| 6,613,910 B2 | 9/2003 | Grubbs et al. |
| 6,620,955 B1 | 9/2003 | Pederson et al. |
| 6,624,338 B2 * | 9/2003 | Commereuc et al. ......... 585/647 |
| 6,696,597 B2 | 2/2004 | Pederson et al. |
| 6,759,537 B2 | 7/2004 | Grubbs et al. |
| 6,794,534 B2 | 9/2004 | Grubbs et al. |
| 6,803,429 B2 | 10/2004 | Morgan et al. |
| 6,818,586 B2 | 11/2004 | Grubbs et al. |
| 6,838,489 B2 | 1/2005 | Bell et al. |
| 6,884,859 B2 | 4/2005 | Grubbs et al. |
| 6,900,347 B2 | 5/2005 | Paulson et al. |
| 6,921,735 B2 | 7/2005 | Hoveyda et al. |
| 6,921,736 B1 | 7/2005 | Nolan et al. |
| 6,946,533 B2 | 9/2005 | Grubbs et al. |
| 6,962,729 B2 | 11/2005 | Tokas et al. |
| 6,987,154 B2 | 1/2006 | Choi et al. |
| 7,026,495 B1 | 4/2006 | Pederson et al. |
| 7,034,096 B2 | 4/2006 | Choi et al. |
| 7,109,348 B1 | 9/2006 | Nolan |
| 7,119,216 B2 | 10/2006 | Newman et al. |
| 7,176,336 B2 | 2/2007 | Maughon et al. |
| 7,205,424 B2 | 4/2007 | Nolan |
| 7,285,593 B1 | 10/2007 | Giardello et al. |
| 7,314,904 B2 | 1/2008 | Nadolsky et al. |
| 7,329,758 B1 | 2/2008 | Grubbs et al. |
| 7,365,140 B2 | 4/2008 | Piers et al. |
| 7,507,854 B2 | 3/2009 | Lee et al. |
| 7,598,330 B2 | 10/2009 | Grubbs et al. |
| 7,622,590 B1 | 11/2009 | Nolan et al. |
| 7,812,185 B2 | 10/2010 | Burdett et al. |
| 2002/0095007 A1 | 7/2002 | Larock et al. |
| 2002/0111517 A1 | 8/2002 | Ahlers et al. |
| 2002/0177710 A1 | 11/2002 | Grubbs et al. |
| 2002/0183578 A1 | 12/2002 | Commereuc et al. |
| 2003/0055262 A1 | 3/2003 | Grubbs et al. |
| 2003/0100776 A1 | 5/2003 | Grubbs et al. |
| 2003/0186035 A1 | 10/2003 | Cruce et al. |
| 2003/0236377 A1 | 12/2003 | Choi et al. |
| 2004/0200136 A1 | 10/2004 | Tao et al. |
| 2005/0027136 A1 | 2/2005 | Toor et al. |
| 2005/0070750 A1 | 3/2005 | Newman et al. |
| 2005/0080301 A1 | 4/2005 | Maughon et al. |
| 2005/0154221 A1 | 7/2005 | Lysenko et al. |
| 2005/0261451 A1 | 11/2005 | Ung et al. |
| 2006/0079704 A1 | 4/2006 | Lacombe et al. |
| 2006/0128912 A1 | 6/2006 | Piers et al. |
| 2008/0027194 A1 | 1/2008 | Schrodi |
| 2008/0064891 A1 | 3/2008 | Lee |
| 2009/0217568 A1 | 9/2009 | Murphy et al. |

FOREIGN PATENT DOCUMENTS

| | | |
|---|---|---|
| EP | 1408064 A1 | 4/2004 |
| FR | 2878246 A1 | 5/2006 |
| JP | 56-077243 A | 6/1981 |
| JP | 09-014574 A | 1/1997 |
| SU | 1565872 | 5/1990 |
| WO | WO 96/04289 A1 | 2/1996 |
| WO | WO 99/26949 | 6/1999 |
| WO | WO 99/32604 | 7/1999 |
| WO | WO 00/71554 | 11/2000 |
| WO | WO 01/36368 A2 | 5/2001 |
| WO | WO 02/14376 | 2/2002 |
| WO | WO 02/059066 | 8/2002 |
| WO | WO 02/076920 | 10/2002 |
| WO | WO 02/094748 | 11/2002 |
| WO | WO 03/093215 A1 | 11/2003 |
| WO | WO 2004/062763 | 7/2004 |
| WO | WO 2004/062763 A2 | 7/2004 |
| WO | WO 2005/080455 A2 | 9/2005 |
| WO | WO 2006/052688 A2 | 5/2006 |
| WO | WO 2007/002999 A1 | 1/2007 |
| WO | WO 2007/081987 A2 | 7/2007 |
| WO | WO 2007/103398 A1 | 9/2007 |
| WO | WO 2008/046106 A2 | 4/2008 |
| WO | WO 2008/048522 A1 | 4/2008 |
| WO | WO 2008/063322 A2 | 5/2008 |

OTHER PUBLICATIONS

Miriam L. Kelly et al.; Nutrient Metabolism (Dietary Fatty Acid Sources Affect Conjugated Linoleic Acid Concentrations In Milk From Lactating Dairy Cows); 1998 American Society For Nutritional Sciences; pp. 881-885.

Committee on Biobased Industrial Products, National Research Council, "Biobased Industrial Products: Research and Commercialization Priorities," National Academies Press: Washington, DC, (1999) pp. 17-18.

Donald L. Palmquist, "Milk Fat—It's Good for You! Ruminal Biohydrogenation," Research and Reviews: Dairy 2001Special Circular 182, Ohio State University Extension Bulletin, 1 pg.

McCoy, Michael, "Starting a Revolution," Chemical and Engineering News, Dec. 15, 2003, vol. 81, No. 50, pp. 17-18 (5 pages online).

Anderson et al., "Synthesis and Reactivity of Olefin Metathesis Catalysts Bearing Cyclic (Alkyl)(Amino) Carbenes," Angewandte Chemie International Edition, vol. 46, 2007, pp. 7262-7265.

Baumann et al., "Natural Fats and Oils—Renewable Raw Materials for the Chemical Industry," Angewandte Chemie International Edition in English, vol. 27, 1988, pp. 41-62.

Biermann et al., "New Syntheses with Oils and Fats as Renewable Raw Materials for the Chemical Industry,", Angewandte Chemie International Edition, vol. 39, 2000, pp. 2206-2224.

Boelhouwer et al., "Metathesis Reactions of Fatty Acid Esters," Progress of Lipid Research, Pergamon Press, vol. 24, No. 3, 1985, pp. 243-267.

Choi et al., "Olefin Metathesis Involving Ruthenium Enoic Carbene Complexes," Journal of the American Chemical Society, vol. 123, No. 42, 2001, pp. 10417-10418.

Connon et al., "A Solid-Supported Phosphine-Free Ruthenium Alkylidene for Olefin Metathesis in Methanol and Water," Bioorganic & Medical Chem Letters, vol. 12, No. 14, 2002, pp. 1873-1876.

Dunne et al., "A Highly Efficient Olefin Metathesis Initiator: Improved Synthesis and Reactivity Studies," Tetrahedron Letters, vol. 44, No. 13, 2003, pp. 2733-2736.

Erhan et al. , "Drying Properties of Metathesized Soybean Oil," Journal of American Oil Chemists' Society, AOCS Press, vol. 74, No. 6, 1997, pp. 703-706.

Lavallo, "Stable Cyclic (Alkyl)(Amino) Carbenes as Rigid or Flexible, Bulky, Electron-Rich Ligands for Transition-Metal Catalysts: A Quaternary Carbon Atom Makes the Difference," Angewandte Chemie Int. Ed., vol. 44, 2005, pp. 5705-5709.

Maynard et al., "Purification Technique for the Removal of Ruthenium from Olefin Metathesis Reaction Products," Tetrahedron Letters, vol. 40, No. 22, 1999, pp. 4137-4140.

Mol, "Applications of Olefin Metathesis in Oleochemistry: An Example of Green Chemistry," Green Chemistry, Royal Society of Chemistry, Cambridge, GB, vol. 4, 2002, pp. 5-13.

Mol et al., "Metathesis in Oleochemistry," J Braz Chem Soc, vol. 9, No. 1, 1998, pp. 1-11.

Mol, "Catalytic Metathesis of Unsaturated Fatty Acid Esters and Oils," Topics in Catalysis, vol. 27, No. 1-4, 2004, pp. 97-104.

Patel et al., "High conversion and productive catalyst turnovers in cross-metathesis reactions of natural oils with 2-butene", *Green Chemistry*, 2006, vol. 8, pp. 450-454.

Refvik et al., "Ruthenium-Catalyzed Metathesis of Vegetable Oils," Journal of American Oil Chemists' Society, AOCS Press, vol. 76, No. 1, 1999, pp. 93-98.

Schneider et al., "Synthesis of Highly Substituted Cyclopentane and Tetrahydrofuran Derivatives by Crossed Olefin Metathesis," Angewandte Chemi International Edition, vol. 35, No. 4, 1996, pp. 411-412.

Tian et al., "Model Studies and the ADMET Polymerization of Soybean Oil," Journal of American Oil Chemists' Society, AOCS Press, vol. 79, No. 5, 2002, pp. 479-488.

\* cited by examiner

METHOD FOR MAKING INDUSTRIAL CHEMICALS

CROSS REFERENCE TO RELATED APPLICATION

This is the U.S. National Stage of International Application No. PCT/US2004/000841, filed Jan. 13, 2004, which in turn claims the benefit of U.S. provisional application No. 60/439,959, filed Jan. 13, 2003, which is incorporated herein by reference.

FIELD

This disclosure concerns a process for producing industrial organic chemicals, with one embodiment comprising isomerization of sites of unsaturation, such as by enzyme-mediated isomerization of olefins, particularly fatty acids or fatty acid derivatives, in combination with metathesis chemistry.

BACKGROUND

Organic chemicals used to produce numerous industrial products, such as paints, solvents, synthetic fibers and plastics, currently are synthesized primarily from petroleum-based products. Moreover, the major portion of pharmaceuticals and fine chemicals also are manufactured from petroleum-derived organic chemicals. Indeed, of the more than one hundred million tons of fine, specialty, intermediate and commodity chemicals produced annually in the United States, only ten percent of these chemicals are biobased, i.e., produced from renewable resources. Committee on Biobased Industrial Products, *Biobased Industrial Products: Research and Commercialization Priorities*, National Academies Press: Washington, D.C., 1999, pp. 17,18. There is an increasing need to replace petroleum-derived chemicals with chemicals derived from renewable resources.

Unsaturated compounds, such as alkenes (which also are referred to herein as olefins), are particularly important chemical feedstocks for producing various products, including polyethylene, polypropylene and polybutylene polymers. The properties of such polymers are modified by copolymerization with different unsaturated chemicals. For example, linear low-density polyethylene (LLDPE) is produced by copolymerizing ethylene and 1-octene. Known processes for producing 1-octene from petroleum-based sources, such as Fischer-Tropsch processes or SHOP-type ethylene oligomerization processes, are inefficient and result in mixtures of oligomerization products that are produced in statistical proportions. Hence, large quantities of undesired materials are produced. As a result, there currently is a shortage of 1-octene, and LLDPE production is constrained by the limited supply of 1-octene.

A further disadvantage associated with current processes is that pollutants are released during extraction and processing of coal and petroleum, posing a number of potential hazards to the environment and human health. Thus, in addition to economic influences, increasing environmental and health concerns provide an impetus for developing biobased products from renewable resources to replace petroleum-based products.

A potential method for forming unsaturated industrial chemicals is metathesis chemistry. Metathesis often involves reacting two different compounds by interchanging atoms or groups of atoms between two molecules. The olefin metathesis reaction can be thought of as a reaction in which carbon-carbon double bonds in an olefin are broken and rearranged in a statistical fashion. An example of alkene metathesis is illustrated in Scheme 1.

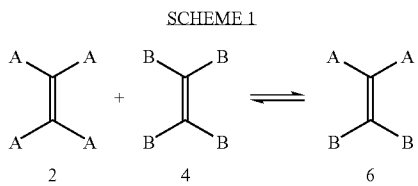

SCHEME 1

In recent years, with the development of new, well-defined, functional group-tolerant metathesis catalysts, metathesis chemistry has been applied to polymer chemistry and complex total syntheses. See, for example, Fürstner, A. Olefin Metathesis and Beyond. *Angew. Chem., Int. Ed. Engl.* 2000, 39, 3012-3043.

Newman et al., PCT publication number WO 02/076920 (Newman), disclose a process for metathesis of unsaturated fatty acid esters or unsaturated fatty acids with small chain olefins. Newman discloses "contacting an unsaturated fatty acid ester or an unsaturated fatty acid . . . with ethylene in the presence of a metathesis catalyst . . . " Newman, page 5, line 22-24. Newman states that in a "most preferred embodiment related thereto, the unsaturated fatty acid is oleic acid; the lower olefin is ethylene; and the olefinic metathesis products include 1-decene and 9-decenoic acid." Newman, page 5, line 32-page 6, line 2. Newman does not, however, disclose any method for isomerizing fatty acids or fatty acid derivatives, nor does Newman teach conjugated linoleic acid or a method for its production. Newman also does not disclose making 1-octene.

Thus, for the reasons stated above, new methods for converting renewable resources into industrial chemicals, such as 1-octene, are desired.

SUMMARY

According to disclosed embodiments of the present process, industrially important, unsaturated hydrocarbons are produced from renewable resources. In particular embodiments the renewable resources are fatty acids or fatty acid derivatives. Fatty acids having at least one site of unsaturation are readily available from vegetable oils including, without limitation, soybean, castor bean, dehydrated castor bean, corn, cucumber, poppyseed, safflower, flaxseed, rapeseed, lesquerella, linseed, grapeseed, sunflower, walnut, pumpkin, cottonseed, meadowfoam, mustard seed, peanut, perilla, tall, tung and sesame oils. In certain embodiments processed oils, such as blown oils, are the source of fatty acids. While vegetable oils are preferred sources of fatty acids for practicing disclosed embodiments of the present process, fatty acids also are available from animal fats including, without limitation, lard and fish oils, such as sardine oil and herring oil, and the like. As noted above, in certain embodiments a desired fatty acid or fatty acid precursor is produced by plant or animal found in nature. However, particular fatty acids or fatty acid precursors are advantageously available from genetically modified organisms, such as a genetically modified plant. Such genetically modified organisms are designed to produce a desired fatty acid or fatty acid precursor biosynthetically or to produce increased amounts of such compounds.

One disclosed embodiment of the present process comprises providing an unsaturated compound, such as a conjugated linoleic acid (for example, Δ9,11-octadecadienoic acid), and contacting the compound with a metathesis catalyst to produce a desired lower olefin. Alternatively, disclosed embodiments comprise providing an unsaturated compound, such as a fatty acid or fatty acid derivative, isomerizing a site of unsaturation in the fatty acid or fatty acid derivative to produce an isomerized fatty acid or fatty acid derivative, and then contacting the isomerized fatty acid or fatty acid ester with a lower olefin or alkyne in the presence of a metathesis catalyst. As used herein, "lower" typically refers to compounds having 20 or fewer carbon atoms, and more typically from 1 to about 10 carbon atoms. For the metathesis reaction, the contacting step is performed under conditions that provide at least one unsaturated product, the unsaturated product being an alkene, an alkyne or both. Typically in this embodiment, the unsaturated fatty acid derivative subjected to metathesis is a diene; however, monounsaturated fatty acids as well as fatty acids having two or more sites of unsaturation can be used. In one aspect of the method, monounsaturated fatty acids are produced from polyunsaturated fatty acids.

The isomerized fatty acid or fatty acid ester can be produced by isomerization of a fatty acid or fatty acid ester with or without subsequent esterification or transesterification. Isomerization can be catalyzed by biochemical or chemical techniques. For example, an isomerase enzyme, such as a linoleate isomerase, can be used to isomerize linoleic acid from the cis 9, cis 12 isomer to the cis 9, trans 11 isomer. This isomerization process is stereospecific, however, nonstereospecific processes can be used because both cis and trans isomers are suitable for metathesis. For example, an alternative process employs a chemical isomerization catalyst, such as an acidic or basic catalyst, can be used to isomerize an unsaturated fatty acid or fatty acid derivative having a site of unsaturation at one location in the molecule into an isomerized, unsaturated fatty acid or fatty acid derivative having a site of unsaturation at a different location in the molecule. Metal or organometallic catalysts also can be used to isomerize an unsaturated fatty acid or fatty acid derivative. For example, nickel catalysts are known to catalyze positional isomerization of unsaturated sites in fatty acid derivatives. Similarly, esterification, transesterification, reduction, oxidation and/or other modifications of the starting compound or products, such as a fatty acid or fatty acid derivative, can be catalyzed by biochemical or chemical techniques. For example, a fatty acid or fatty acid derivative can be modified by a lipase, esterase, reductase or other enzyme before or after isomerization.

In a particular disclosed embodiment involving the conversion of linoleic acid, or a linoleic acid derivative, into the cis 9, trans 11 isomer using linoleate isomerase, the cis 9, trans 11 isomer is then subjected to metathesis conditions in the presence of ethylene. The resulting metathesis reaction yields industrially useful products, including 1,3-butadiene, 1-octene and 9-decenoic acid or derivatives thereof Particular derivatives include 9-decenoate esters, such as lower alkyl, 9-decenoate esters.

In another disclosed embodiment of the method an enzyme, such as an isomerase, is used in an immobilized reactor, such that a metathesis substrate can be produced continuously. In a working embodiment, linoleate isomerase is bound to a solid support and an immobilized enzyme reactor is constructed using isolated, bound linoleate isomerase.

In still another disclosed embodiment of the present method, an immobilized metathesis catalyst is used. Immobilizing the metathesis catalyst allows flow conditions to be used for the metathesis process and can aid catalyst recycling.

DETAILED DESCRIPTION

Figure 1:
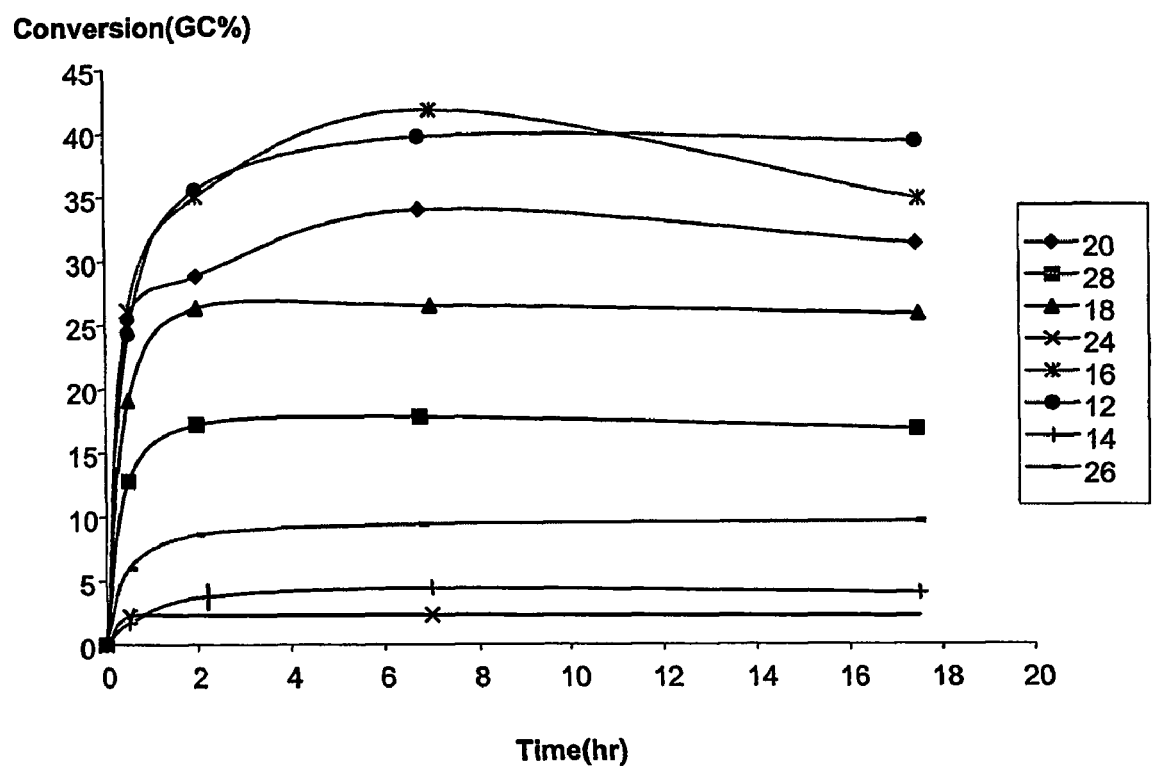
FIG. 1 is a graph of percent conversion versus time (hours) illustrating the time course of the conversion of Δ9,11-octadecadienoic acid to 9-methyldecenoate via ethenolysis in the presence of various metathesis catalysts.
Figure 2:
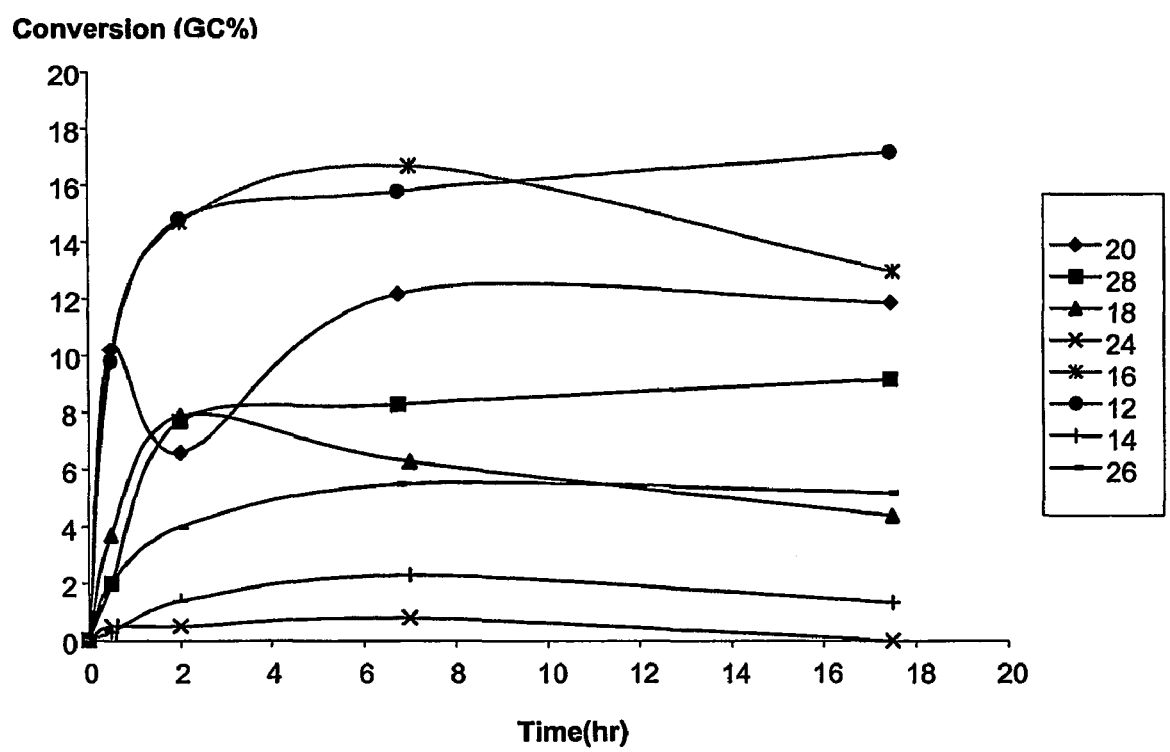
FIG. 2 is a graph of percent conversion versus time (hours) illustrating the time course of the conversion of Δ9,11-octadecadienoic acid to 1-octene via ethenolysis in the presence of various metathesis catalysts.

According to disclosed embodiments of the present process, industrial chemicals can be produced from renewable resources, and agricultural crops can be used as chemical feedstocks for producing such industrial chemicals. While the present method is not limited to using fatty acids as a precursor for the production of industrial chemicals, particular disclosed embodiments of the process use fatty acids and fatty acid derivatives that are available from renewable resources. As used herein, the term "fatty acid" generally refers to any carboxylic acid derived from fats by hydrolysis, especially those found in animal and vegetable oils. Typically, but not necessarily, fatty acids are straight-chain hydrocarbons having from about 3 to about 20 carbon atoms. It is also understood that certain compounds are equivalent to fatty acids, for example, fatty acids and the corresponding salts and esters can be readily interconverted. Generally, ester derivatives employed in the method are lower alkyl esters, including without limitation, methyl, ethyl, propyl, isopropyl, butyl, tert-butyl, sec-butyl, iso-butyl esters and the like. Furthermore, fatty acid derivatives, which include any compound or portion of a compound that is derived from or is theoretically derivable from a fatty acid, include, without limitation, esterified, dehydrated, reduced and oxidized fatty-acid derivatives. For example, fatty acids can be reduced at the carboxylate or at a site of unsaturation to provide fatty acid derivatives that are useful for producing industrial chemicals according to the disclosed method.

According to embodiments of the disclosed process a precursor fatty acid is isolated, and the fatty acid is modified to give a fatty-acid derivative. The fatty-acid derivative is then converted into one or more industrial chemicals via at least one metathesis reaction. In certain aspects of the process a fatty acid is subjected directly to metathesis conditions without any chemical modifications. The products of such a direct metathesis process can be optionally chemically modified to produce desired derivatives. Embodiments of each step of the present process are described in further detail below.

I. Renewable Resources

Raw materials for biobased production of industrial chemicals include oils, such as vegetable oils and animal fats. Few industrially important chemicals currently can be made directly by metathesis of such raw materials with an alkene or alkyne. To solve this problem, embodiments of the present process provide a method for producing industrial chemicals from these raw materials by isomerizing the raw material prior to metathesis. For example, there currently is a shortage of 1-octene, but 1-octene is not directly available via metathesis of any common fatty acid.

According to a particular embodiment of the present method 1-octene can be produced from renewable resources by combining an isomerization process and a metathesis process. For example, linoleic acid can be isomerized to a conjugated linoleic acid (CLA). CLA is a generic term referring to several conjugated isomers of linoleic acid. Any CLA having olefins (cis or trans) at the 9 and 11 positions is useful for producing the industrially useful chemicals 1-octene, butadiene and 9-decenoic acid.

Historically, conjugated linoleic acid has been produced by heating linoleic acid in the presence of a strongly basic material, such as a hydroxide. This procedure provides a mixture of conjugated positional isomers, as well as mixtures of cis and trans double bonds. An embodiment of the present process exploits the selectivity of an enzymatic transformation, which produces CLA having olefins at the 9 and 11 positions substantially free of other CLA isomers.

Unsaturated fatty acids are named herein either according to their common name, systematic name, or shorthand by carbon number, followed by the number and position of any double bonds, as numbered from the carboxylate carbon. For example, structure 8 (Scheme 2), having the common name linoleic acid, has eighteen carbon atoms and two double bonds, the first between the ninth and tenth carbon and the second between the twelfth and thirteenth carbons. Thus, linoleic acid 8 is named systematically as Δ9,12-octadecadienoic acid, where "octadeca" indicates that there are 18 carbon atoms, "dien" indicates that there are two double bonds, and Δ9,12 indicates the alkene carbons. The "oic" suffix indicates that the compound is the free carboxylic acid, rather than an esterified carboxylic acid. The shorthand system for naming linoleic acid 8 is 18:2Δ9,12, where 18 indicates the number of carbons, 2 indicates the number of double bonds, and Δ9,12 indicates the position of the two double bonds on the carbon chain.

With reference to Scheme 2, Δ9,12-octadecadienoic acid 8 is isomerized to Δ9,11-octadecadienoic acid 10 in the presence of an enzyme, linoleate isomerase. In another embodiment of the process a monoene fatty acid, such as a vaccenic acid isomer having a C-11 olefin is produced by an isomerization reaction, a hydrogenation reaction, or both. For example, in one aspect of the method, a diene having a C-11 olefin and another olefin is selectively reduced enzymatically to provide Δ11-octadecenoic acid. This transformation is performed, for example, by rumen microorganisms. See, Kelly, et al. *J. Nutr.* 1998, 128, 881-885, which is incorporated herein by reference. Such vaccenic acid isomers also are useful intermediates for producing 1-octene via metathesis.

According to disclosed embodiments of the present process using an enzyme to isomerize sites of unsaturation, the enzyme can be an isolated enzyme or can be used as a whole cell preparation. "Isolated" refers to an enzyme partially or substantially completely purified. Isolating the enzyme can increase enzyme activity. Examples of isolated enzymes include crude extracts, membrane-bound enzymes, soluble enzymes, recombinantly produced enzymes, solubilized enzymes and the like. In particular embodiments enzymes may be solubilized or stabilized by complexation with lipids, proteins, artificial membranes, and combinations thereof.

In embodiments that use linoleate isomerase, the enzyme can be isolated or used in a whole cell according to the procedure disclosed by Rosson et al. in PCT publication number WO 99/32604. Certain embodiments can use whole cells to produce Δ9,11-octadecadienoic acid according to the fermentation protocol disclosed by Pariza and Yang in U.S. Pat. No. 6,060,304. Published PCT publication number WO 99/32604 and U.S. Pat. No. 6,060,304 are incorporated herein by reference.

In certain embodiments the enzyme or cell having the enzyme may be immobilized. For example, enzymes can be immobilized by a technique selected from the group consisting of matrix entrapment, microencapsulation, adsorption, and covalent binding. Cells expressing the enzyme can be immobilized by crosslinking to a surface with a bifunctional or multifunctional crosslinking agent or can be bound to a surface by a noncovalent interaction, such as a protein-ligand interaction. In such embodiments, a flow reactor can be used to perform the isomerization reaction.

An alternative route to compound 10 employs Δ9-octadecenoic acid (not shown) and exploits a Δ11-desaturase enzyme to produce compound 10. Alternatively, another route employs the saturated starting material, octadecanoic acid and a Δ11-desaturase enzyme to produce Δ11-octadecenoic acid (not shown), which is commonly known as vaccenic acid. Such a route also can use a Δ9-desaturase enzyme to produce compound 10. Δ11-Octadecenoic acid is a useful intermediate for producing 1-octene, and this fatty acid also can be produced by isomerization of readily available Δ9,12-octadecadienoic acid to Δ9,11-octadecadienoic acid, followed by selective, enzymatic reduction of the Δ9 double bond.

II. Metathesis

Any known or future-developed metathesis catalyst may be used, alone or in combination with one or more additional

SCHEME 2

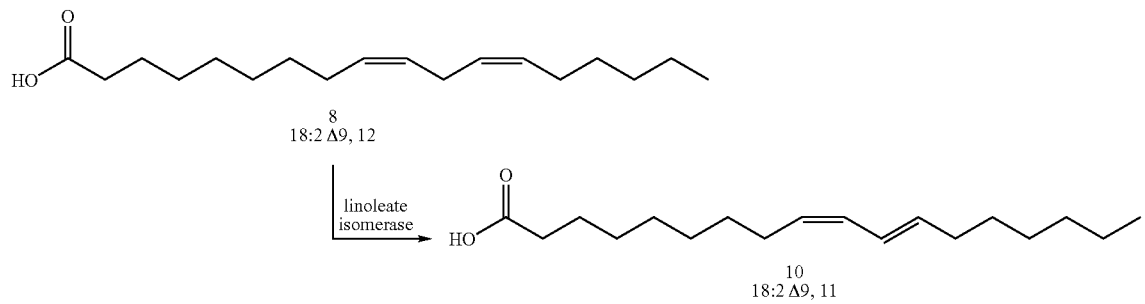

8
18:2 Δ9, 12 linoleate isomerase 10
18:2 Δ9, 11 catalysts, in accordance with embodiments of the present method. Typical metathesis catalysts used for disclosed embodiments include metal carbene catalysts based upon transition metals, such as ruthenium. Exemplary ruthenium-based metathesis catalysts include those commercially available catalysts represented by structures 12 (commonly referred to as Grubbs's catalyst), 14 and 16.

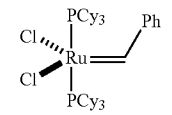

12

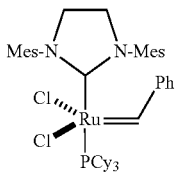

14

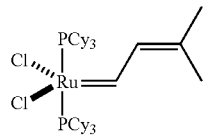

16

Structures 18-28, illustrated below, represent additional useful ruthenium-based metathesis catalysts. Techniques for using catalysts 12-28, as well as additional related metathesis catalysts are disclosed in PCT publication numbers WO 99/26949, WO 00/71554, WO 02/14376, and in U.S. patent application publication number 2002/0177710. Each of these patent publications is incorporated herein by reference in its entirety.

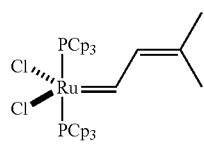

18

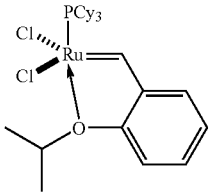

20

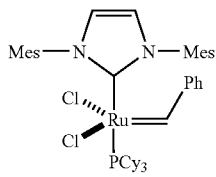

22

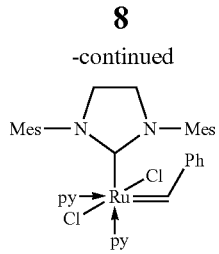

24

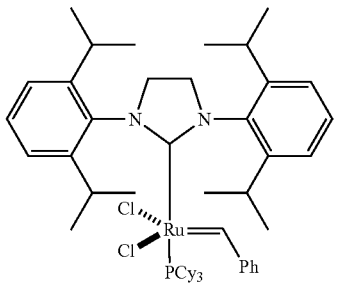

26

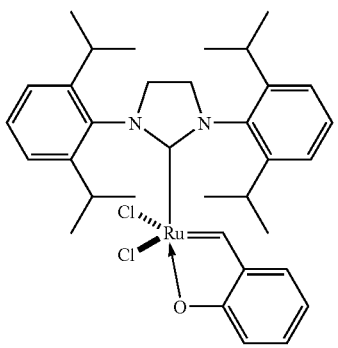

28

Additional metathesis catalysts include, without limitation, metal carbene complexes selected from the group consisting of molybdenum, osmium, chromium, rhenium, tungsten and tungsten carbene complexes. The term "complex" refers to a metal atom, such as a transition metal atom, with at least one ligand or complexing agent coordinated or bound thereto. Such a ligand typically is a Lewis base in metal carbene complexes useful for alkene, alkyne or alkene-metathesis. Typical examples of such ligands include phosphines, halides and stabilized carbenes. Some metathesis catalysts employ plural metals or metal co-catalysts. For example, German patent publication number A1-282594, which is incorporated herein by reference, discloses a catalyst comprising a tungsten halide, a tetraalkyl tin compound, and an organoaluminum compound.

An immobilized catalyst can be used for the metathesis process. See, for example, Blechert, et al. Synthesis and Application of a Permanently Immobilized Olefin Metathesis Catalyst. *Angew. Chem. Int. Ed. Engl.* 2000, 39, 3898-3901, incorporated herein by reference. Such an immobilized catalyst can be used in a flow process as is known to those of ordinary skill in the art. An immobilized catalyst can simplify purification of products and recovery of the catalyst, so that recycling the catalyst is convenient.

The metathesis process for producing industrial chemicals can be conducted under any conditions adequate to produce the desired metathesis product or products. For example, stoichiometry, atmosphere, solvent, temperature and pressure can be selected to produce a desired product and to minimize undesirable byproducts. The metathesis process typically is conducted under an inert atmosphere. Similarly, if an olefin or alkyne reagent is supplied as a gas, an inert gaseous diluent can be used. The inert atmosphere or inert gaseous diluent typically is an inert gas, meaning that the gas does not interact with the metathesis catalyst to substantially impede catalysis. For example, particular inert gases are selected from the group consisting of helium, neon, argon, nitrogen and combinations thereof. In certain embodiments a gaseous, lower unsaturated reagent is employed. In such embodiments the lower unsaturated reagent may be used with or without a gaseous diluent.

Similarly, if a solvent is used, the solvent chosen typically is substantially inert with respect to the metathesis catalyst. For example, substantially inert solvents include, without limitation, aromatic hydrocarbons, such as benzene, toluene, xylenes, and the like; halogenated aromatic hydrocarbons, such as chlorobenzene and dichlorobenzene; aliphatic solvents, including pentane, hexane, heptane, cyclohexane, and the like; and chlorinated alkanes, such as dichloromethane, chloroform, dichloroethane, and the like.

In certain embodiments, a ligand is added to the metathesis reaction mixture. Typically the ligand is a molecule that stabilizes the catalyst, thereby providing an increased turnover number for the catalyst. In some cases the ligand can alter reaction selectivity and product distribution. Examples of ligands that can be used include Lewis base ligands, such as, without limitation, trialkylphosphines, for example tricyclohexylphosphine and tributyl phosphine; triarylphosphines, such as triphenylphosphine; diarylalkylphosphines, such as, diphenylcyclohexylphosphine; pyridines, for example 2,6-dimethylpyridine, 2,4,6-trimethylpyridine; as well as other Lewis basic ligands, such as phosphine oxides and phosphinites.

Using currently known catalysts, the metathesis processing temperature is largely a rate-dependent variable where the temperature is selected to provide a desired product at an acceptable production rate. The selected temperature typically is greater than about −40° C., typically greater than about −20° C., more typically greater than about 0° C., and most typically greater than about 20° C. Generally, the process temperature is less than about 150° C., and preferably less than about 120° C. Thus, a currently preferred temperature range for the metathesis reaction is from greater than about 20° C. to about 120° C. Lower temperatures can be used, for example, to minimize the production of undesired impurities or to favor a particular reaction pathway. Examples of using temperature to control reaction rate and to vary reaction products are disclosed in PCT publication number WO 02/094748, which is incorporated herein by reference.

The metathesis process can be conducted under any pressure of gaseous alkene, alkyne and/or diluent. The total pressure generally is greater than about 30 kPa, and more typically is greater than about 100 kPa. Generally, the total pressure is less than about 7,000 kPa, and more typically is less than about 3,000 kPa. Therefore, a likely useful pressure range for the metathesis process conducted under pressure is from about 100 kPa to about 3,000 kPa.

Any useful amount of the selected metathesis catalyst can be used in the current process. If the catalyst has a relatively high turnover number, the molar ratio of the metathesis process precursor, such as an unsaturated fatty acid or fatty acid derivative, to the catalyst can be as high as about 10,000,000 to 1, but more typically is less than about 500,000 to 1. The molar ratio of the unsaturated fatty acid or fatty acid derivative to the catalyst typically is greater than about 5 to 1, and preferably greater than about 50 to 1, and more preferably greater than about 100 to 1. Several working examples used a substrate-to-catalyst molar ratio of 25 to 1.

III. Production of Industrial Chemicals

Industrial chemicals typically are derived from petroleum resources. Using the present process a desired industrial chemical may be produced from renewable resources by selecting an appropriate unsaturated precursor fatty acid and an appropriate unsaturated reagent. This process is illustrated retrosynthetically in Scheme 3.

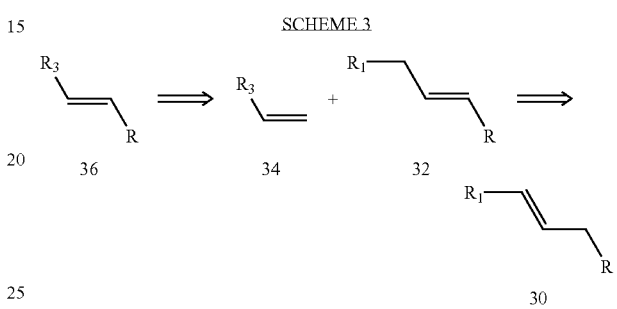

With reference to Scheme 3, structure 36 represents a desired compound and structures 32 and 34 represent precursors to 36. Compounds having the structures 32 and 34 can be converted into a compound having the structure 36 by a metathesis reaction. Structure 32 can be obtained from renewable resource 30 using an isomerization reaction.

In preferred embodiments, more than one industrially useful product is produced. As illustrated retrosynthetically in Scheme 4, two product compounds represented by structures 36 and 38 may be formed.

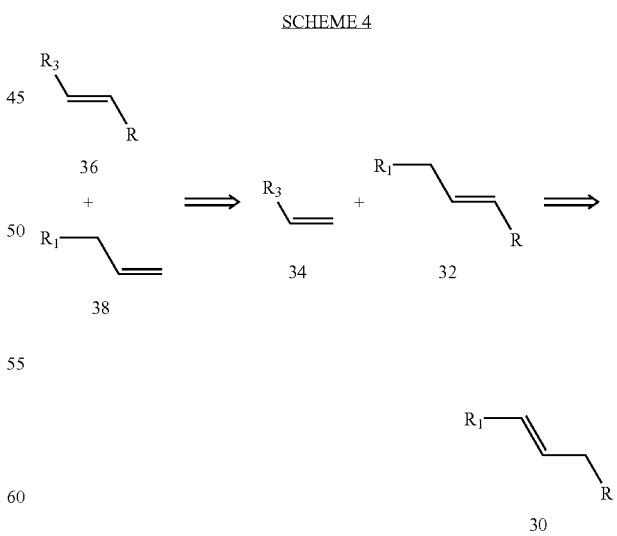

Alternatively, three or more products may be produced. For example, polyunsaturated fatty acids having two or more unsaturated sites yield three or more products according to embodiments of the present method. See Scheme 5 below.

SCHEME 5

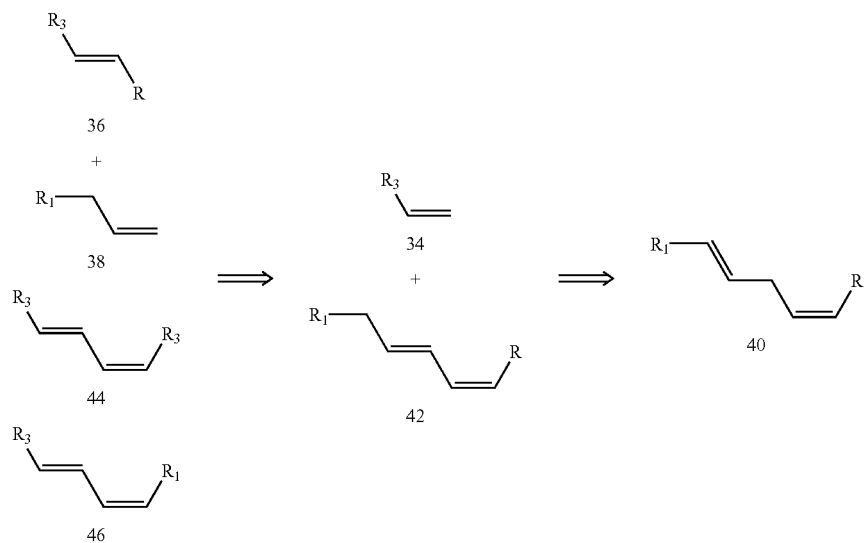

Embodiments of the present process as illustrated by Schemes 3-5 are particularly useful for producing chemicals that are not directly available from readily available, renewable resources via a metathesis reaction. A particularly valuable class of industrial chemicals comprises the α-olefins. α-olefins are terminal alkenes, and primarily are used as comonomers with a second olefin for producing polyolefins.

A particularly useful process for producing α-olefins includes ethylene as a starting material. For example, with reference to Schemes 3-5 above, $R_3$ is hydrogen and compound 34 is ethylene.

With reference to Schemes 3-5, disclosed embodiments of the present process generally employ an olefin reagent, such as the compound represented by structure 34 in Schemes 3-5. However, in particular embodiments an alkyne reagent may replace the olefin reagent. In such embodiments a 1,3-diene derivative is formed via alkene-alkyne (enyne) metathesis. The olefin or alkyne reagent reacts with a fatty acid to give at least one desired chemical.

In preferred embodiments of the present process, the olefin or alkyne is a lower unsaturated reagent, such as a lower olefin or alkyne. By definition the lower unsaturated reagent has at least one carbon-carbon double or triple bond, and may have plural carbon-carbon double or triple bonds. The lower olefin can contain an internal double or triple bond, a terminal-double or triple bond, or both. Double bonds can be tetra-, tri-, di-, or monosubstituted. Suitable substituents for the lower unsaturated reagent may include, without limitation, aliphatic, aromatic, hydroxy, ether, keto, aldehyde, and halogen functional groups. Preferably, aliphatic substituents are lower alkyl substituents. Preferred lower olefins include ethylene, propylene, butene, butadiene, pentene, hexene, and isomers thereof. Preferred lower alkynes include acetylene and propyne.

Yields for disclosed embodiments of the present process are defined as mole percentage with respect to the fatty acid precursor. Typically the yield of at least one unsaturated product of the metathesis process is greater than about 35 mole percent, and more typically greater than about 50 mole percent.

With reference to Scheme 6, 1-octene is produced according to an embodiment of the present process beginning with a conjugated linoleate, such as methyl linoleate derivative 48. Compound 48 can be prepared by isomerization of linoleic acid (18:2Δ9,12) to the conjugated linoleic acid isomer 10 (18:2Δ9,11) as shown in Scheme 2. Esterification of 10 with methanol gives 48. Conjugated methyl linoleate derivative 48 is then contacted with a metathesis catalyst in the presence of ethylene to afford 1-octene 50, methyl 9-decenoate 52, and butadiene 54. Alternatively, conjugated linoleic acid isomer 10 may be used directly in the metathesis reaction, without prior esterification, to produce 50, 54, and 9-decenoic acid (not shown).

SCHEME 6

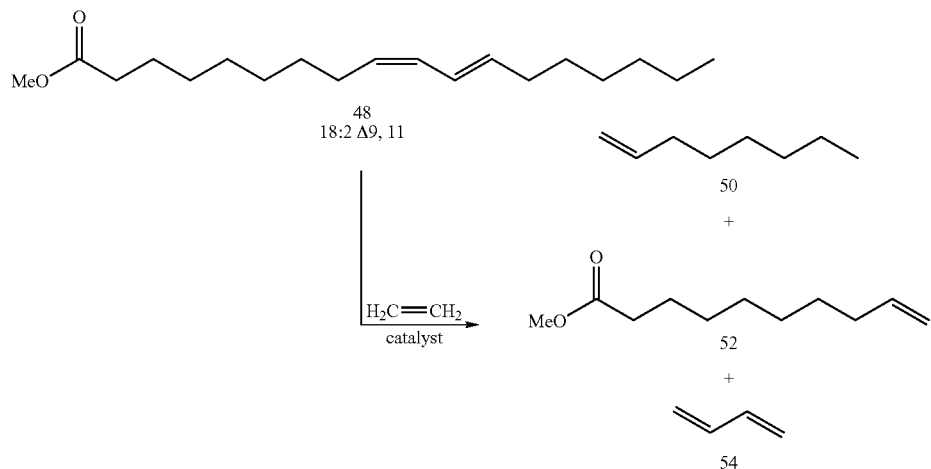

All three illustrated products 50, 52 and 54 of Scheme 6 are industrially useful chemicals. For example, 1-octene 50 is used industrially as a comonomer with ethylene to produce LLDPE. Methyl 9-decenoate 52 can be used to produce azelaic acid, decanol, decanoic acid, aminodecanoic acid and other industrially useful compounds. These compounds are used industrially to produce nylon and thermoset resins as well as other products. Butadiene 54 is used industrially in rubber and latex polymer production.

Scheme 7 illustrates an alternative embodiment for producing vaccenic acid derivative 56 (18:1Δ11) from linoleic acid derivative 48 (18:2Δ9,11) via a regioselective reduction reaction. Subsequent metathesis with ethylene yields 1-octene 50 and methyl 11-dodecenoate 58. As in Scheme 6, an alternative embodiment employs linoleic acid isomer 10 in place of methyl ester 48. In this embodiment the corresponding free acids of compounds 56 and 58 are produced.

SCHEME 7

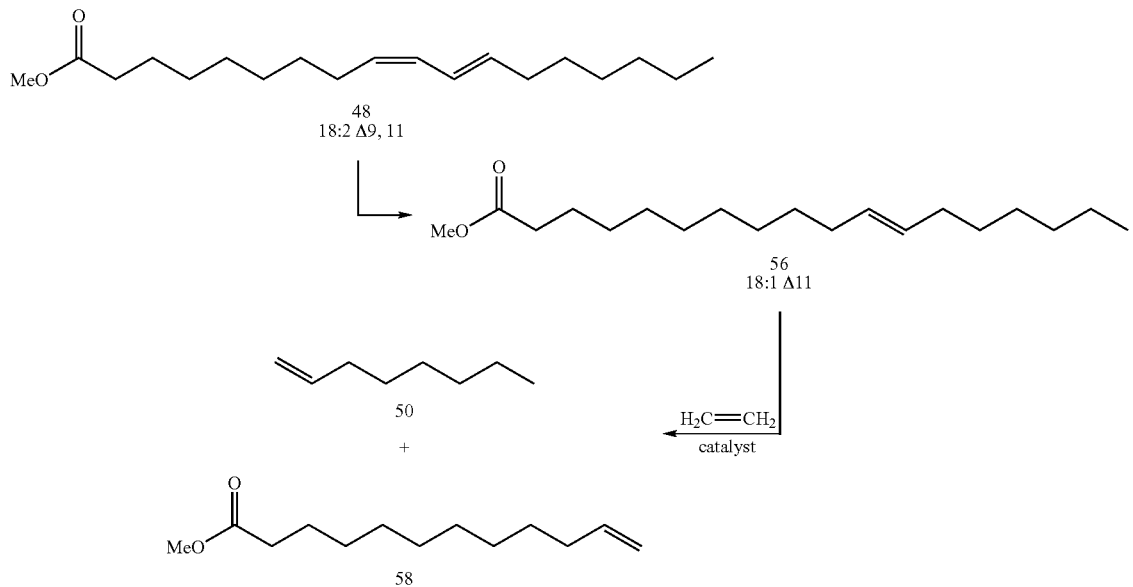

Scheme 8 illustrates an embodiment of the disclosed method suitable for producing the useful industrial chemical methyl-9-decenoate. In this embodiment oleic acid derivative 62 is produced from linoleic acid derivative 60 (18:2Δ9,12) via a regioselective enzymatic reduction process. Subsequent metathesis with ethylene yields 1-decene 64 and methyl-9-decenoate 66. As in other examples of the method, the corresponding fatty acid of compound 60 can be used directly to afford 9-decenoic acid.

be added, for example, as a purified material having a purity of about 99%, or as a component of another oil, such as soybean oil, which has a concentration of about 50% linoleic acid. Alternatively, linoleic acid can be dissolved in a cosolvent, such as propylene glycol. Typically, linoleic acid is added at a concentration of between about 0.5 and 4 g/L by adding several aliquots of smaller linoleic acid amounts. Higher CLA product concentrations can be obtained by adding cells in successive steps as the reaction proceeds. Under

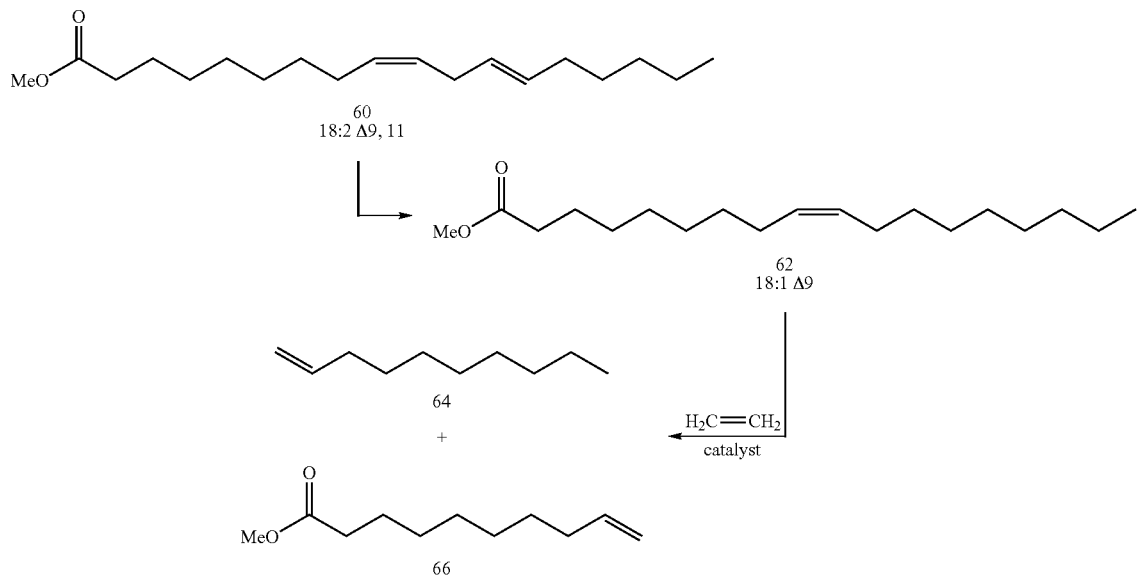

EXAMPLES

The following examples are provided to illustrate certain particular embodiments of the disclosure. It should be understood that additional embodiments, not limited to these particular features described, are consistent with the following examples.

Example 1

This example describes a method for producing Δ9,11-conjugated linoleic acid 10 (CLA) from linoleic acid. The cells used herein, *Lactobacillus reuteri* PYR8 (ATCC Accession No. 55739, deposited on Feb. 15, 1996 with the American Type Culture Collection (ATCC), 10801 University Boulevard, Manassas, Va. 20110, USA) are grown on MRS *Lactobacillus* Broth (BBL) in closed containers with limited head space. Large scale cultures were grown (1-2% inoculum) in 2-L bottles without agitation at 37° C. for about 36 to about 40 hours, harvested by centrifugation, washed once with 0.1 M bis-tris, 0.9% NaCl pH 6.0 buffer, and are used immediately or stored at about −80° C.

Cells of *Lactobacillus reuteri* (or another organism carrying the linoleate isomerase gene) are grown in modified AV medium with 40 g/L yeast extract, 20 g/L Hy-soy and 40 g/L glucose to a cell density of about 3-4 g/L dry cell weight. When the cells reach stationary phase, they are harvested and resuspended in breakage buffer at a concentration of between 5 and 20 g dry cell weight per liter. The biotransformation preferably is carried out at a temperature between 4° C. and 8° C. to maintain optimal enzyme activity. The linoleic acid can such conditions using the disclosed linoleic acid concentrations, conversion of linoleic acid to CLA is between 80% and 100% within from about 2 to about 8 hours.

Methyl Δ9,11 octadecadienoate as well as other esters can be prepared from compound 10, which is produced as described above. In one method for preparing such esters, compound 10 is esterified with methanol under Dean-Stark conditions in the presence of 1% sulfuric acid to yield the corresponding methyl ester. After no more water is released, excess methanol is distilled, leaving methyl Δ9,11-octadecadienoate.

Example 2

This example describes a procedure for fatty acid analysis to determine the conversion of linoleic acid to Δ9,11-CLA From the reaction mixture described in Example 1, fatty acids are extracted from about 1 mL to about 2.5 mL aqueous samples with 0.5 mL of 5 M NaCl added. The samples were shaken with 5 mL of a 2:1 mixture of chloroform/methanol in a glass screw cap tube with a Teflon lined cap. The two phases are separated and about 1 to 2 mL of the chloroform layer is removed. The organic layer is dried with $Na_2SO_4$ and concentrated. The concentrated fatty acids are converted to the corresponding methyl esters using the following procedure adapted from Chin et al., *J. Food Composition,* 1992, 5, 185-192: About 6 mL of 4% HCl in methanol preheated to 60° C. is added to the glass tube containing the fatty acid sample. The tube is sealed with a teflon lined cap and incubated in a tube heater at 60° C. for 20 minutes, cooled to room temperature, and 2 mL of water and 3 mL of hexane are added. After shaking, the organic layer is separated, dried with $Na_2SO_4$, and analyzed by gas chromatography.

Example 3

This example describes the production of industrial chemicals from methyl-Δ9,11-octadecenoate via ethenolysis. In a glove box under inert atmosphere, methyl-Δ9,11-octadecenoate produced according to Example 1 (2.95 g; 0.01 mol) was dissolved in dichloromethane to prepare 100 mL of a 0.1 M stock solution. Additionally, a 0.1 M solution of 20 (60 mg; 0.1 mmol) also was prepared in dichloromethane (1 mL). The conjugated methyl linoleate solution (25 mL) was then charged in a Fisher-Porter bottle equipped with a stir bar. The solution of catalyst 20 (100 μL) was added via a microsyringe and a Fisher-Porter bottle's head equipped with a pressure gauge and a dip-tube was adapted on the bottle. The system was sealed and taken out of the glove box to an ethylene line. The vessel was then purged with ethylene (3 times), pressurized to 150 psi (1034 kPa) of ethylene and placed in an oil bath at 30° C. The reaction was monitored by collecting samples via the dip-tube at different reaction times and quenching each sample by addition of a solution of trishydroxymethyl phosphine. The samples were then heated for at least 1 hour at 60° C., washed with distilled water, extracted with hexanes and analyzed by gas chromatography (GC). During the course of the reaction, the following ethenolysis products were observable by GC: 1-octene ($C_8$, Scheme 6, compound 50); 1,3-decadiene ($C_{10}$); methyl 9-decenoate (Scheme 6, compound 52); 7-tetradecene ($C_{14}$); methyl 9,11-dodecadienoate ($C_{12}$), and 1,18-dimethyl 9-octadecenedioate ($C_{18}$). The percentages (%) of these products in the reaction mixture over time are recorded in Table 1.

TABLE 1

| Time (hr) | 50 | $C_{10}$ | 52 | $C_{12}$ | $C_{14}$ | $C_{18}$ | 48 | Impurities |
|---|---|---|---|---|---|---|---|---|
| 0.0 | 0.0 | 0.0 | 0.0 | 0.0 | 0.0 | 0.0 | 98.4 | 1.6 |
| 0.5 | 14.3 | 22.8 | 35.6 | 5.3 | 0.7 | 0.0 | 16.9 | 4.4 |
| 2.0 | 8.5 | 22.1 | 37.4 | 5.5 | 0.6 | 0.0 | 16.7 | 9.2 |
| 6.75 | 13.2 | 23.7 | 36.7 | 8.2 | NI | 0.0 | 16.2 | 2.0 |
| 17.45 | 13.4 | 21.6 | 35.2 | 7.4 | NI | 0.0 | 15.6 | 6.8 |

NI = not integrated

Example 4

This example describes the production of industrial chemicals via ethenolysis using catalyst 12. Using the general procedure and conditions described in Example 2, the ethenolysis of conjugated methyl linoleate catalyzed by catalyst 12 was monitored over time. The percentages (%) of the ethenolysis products in the reaction mixture over time are recorded in Table 2.

TABLE 2

| Time (hr) | 50 | $C_{10}$ | 52 | $C_{12}$ | $C_{14}$ | $C_{18}$ | 48 | Impurities |
|---|---|---|---|---|---|---|---|---|
| 0.0 | 0.0 | 0.0 | 0.0 | 0.0 | 0.0 | 0.0 | 98.4 | 1.6 |
| 0.5 | 12.9 | 20.2 | 32.1 | 7.4 | 0.7 | 0.0 | 19.1 | 7.6 |
| 2.0 | 17.6 | 21.5 | 42.2 | 6.8 | 0.4 | 0.0 | 7.3 | 4.2 |
| 6.75 | 17.8 | 23.2 | 43.7 | 6.9 | 0.5 | 0.0 | 5.9 | 2.0 |
| 17.45 | 19.2 | 20.2 | 43.9 | 5.5 | 0.6 | 0.0 | 6.3 | 4.3 |

Example 5

This example describes the production of industrial chemicals via ethenolysis using catalyst 16. Using the general procedure and conditions described in Example 2, the ethenolysis of conjugated methyl linoleate catalyzed by catalyst 16 was monitored over time. The percentages (%) of the ethenolysis products in the reaction mixture over time are recorded in Table 3.

TABLE 3

| Time (hr) | 50 | $C_{10}$ | 52 | $C_{12}$ | $C_{14}$ | $C_{18}$ | 48 | Impurities |
|---|---|---|---|---|---|---|---|---|
| 0.0 | 0.0 | 0.0 | 0.0 | 0.0 | 0.0 | 0.0 | 98.4 | 1.6 |
| 0.5 | 11.2 | 20.9 | 29.1 | 8.3 | 0.0 | 0.0 | 27.8 | 2.7 |
| 2.0 | 16.6 | 23.2 | 39.4 | 7.7 | 0.0 | 0.0 | 9.6 | 3.5 |
| 7.0 | 17.2 | 23.6 | 42.6 | 7.4 | 0.0 | 0.0 | 7.2 | 2.0 |
| 17.50 | 15.6 | 22.5 | 41.6 | 7.0 | 0.0 | 0.0 | 6.8 | 6.5 |

Example 6

This example describes the production of industrial chemicals via ethenolysis using catalyst 18. Using the same procedure and same conditions as those described in Example 2, the ethenolysis of conjugated methyl linoleate catalyzed by 18 was monitored over time. The percentages (%) of the ethenolysis products in the reaction mixture over time are recorded in Table 4.

TABLE 4

| Time (hr) | 50 | $C_{10}$ | 52 | $C_{12}$ | $C_{14}$ | $C_{18}$ | 48 | Impurities |
|---|---|---|---|---|---|---|---|---|
| 0.0 | 0.0 | 0.0 | 0.0 | 0.0 | 0.0 | 0.0 | 98.4 | 1.6 |
| 0.5 | 4.3 | 18.6 | 22.7 | 6.4 | 0.0 | 0.0 | 44.8 | 3.2 |
| 2.0 | 9.0 | 23.5 | 29.8 | 7.3 | 0.0 | 0.0 | 26.8 | 3.6 |
| 7.0 | 7.3 | 23.6 | 30.6 | 7.9 | 0.0 | 0.0 | 29.4 | 1.2 |
| 17.50 | 5.1 | 23.4 | 30.0 | 7.7 | 0.0 | 0.0 | 28.0 | 5.8 |

Example 7

This example describes the production of industrial chemicals via ethenolysis using catalyst 14. Using the general procedure and conditions described in Example 3, the ethenolysis of conjugated methyl linoleate catalyzed by 14 was monitored over time. The percentages (%) of the ethenolysis products in the reaction mixture over time are recorded in Table 5.

TABLE 5

| Time (hr) | 50 | $C_{10}$ | 52 | $C_{12}$ | $C_{14}$ | $C_{18}$ | 48 | Impurities |
|---|---|---|---|---|---|---|---|---|
| 0.0 | 0.0 | 0.0 | 0.0 | 0.0 | 0.0 | 0.0 | 98.4 | 1.6 |
| 0.5 | 0.4 | 0.7 | 2.0 | 0.5 | 0.7 | 5.8 | 59.7 | 30.2 |
| 2.0 | 1.7 | 1.5 | 4.4 | 0.8 | 0.7 | 5.8 | 55.2 | 29.9 |
| 7.0 | 2.4 | 1.6 | 4.7 | 0.9 | 1.0 | 5.9 | 54.5 | 29.0 |
| 17.50 | 1.6 | 1.6 | 5.0 | 1.5 | 0.7 | 5.4 | 53.0 | 31.2 |

Example 8

This example describes the production of industrial chemicals via ethenolysis using catalyst 26. Using the same procedure and same conditions as those described in Example 3, the ethenolysis of conjugated methyl linoleate catalyzed by 26 was monitored over time. The percentages (%) of the ethenolysis products in the reaction mixture over time are recorded in Table 6.

TABLE 6

| Time (hr) | 50 | $C_{10}$ | 52 | $C_{12}$ | $C_{14}$ | $C_{18}$ | 48 | Impurities |
|---|---|---|---|---|---|---|---|---|
| 0.0 | 0.0 | 0.0 | 0.0 | 0.0 | 0.0 | 0.0 | 98.4 | 1.6 |
| 0.5 | 2.5 | 3.2 | 7.4 | 2.0 | 0.0 | 2.0 | 48.4 | 34.5 |
| 2.0 | 5.0 | 5.0 | 10.6 | 1.1 | 0.0 | 2.8 | 49.1 | 26.4 |
| 6.75 | 5.9 | 5.3 | 10.0 | 1.5 | 0.0 | 3.5 | 47.1 | 26.7 |
| 17.45 | 5.6 | 4.4 | 10.4 | 1.2 | 0.0 | 3.9 | 48.7 | 25.8 |

Example 9

This example describes the production of industrial chemicals via ethenolysis using catalyst 28. Using the general procedure and conditions described in Example 3, the ethenolysis of conjugated methyl linoleate catalyzed by 28 was monitored over time. The percentages (%) of the ethenolysis products in the reaction mixture over time are recorded in Table 7.

TABLE 7

| Time (hr) | 50 | $C_{10}$ | 52 | $C_{12}$ | $C_{14}$ | $C_{18}$ | 48 | Impurities |
|---|---|---|---|---|---|---|---|---|
| 0.0 | 0.0 | 0.0 | 0.0 | 0.0 | 0.0 | 0.0 | 98.4 | 1.6 |
| 0.5 | 7.4 | 8.6 | 18.8 | 3.3 | 1.0 | 0.0 | 50.3 | 10.6 |
| 2.0 | 8.8 | 9.2 | 19.7 | 4.6 | 1.0 | 1.1 | 51.0 | 4.6 |
| 6.75 | 9.0 | 9.5 | 19.4 | 4.8 | 0.0 | 1.7 | 49.4 | 6.2 |
| 17.45 | 10.2 | 8.6 | 18.6 | 4.0 | 0.0 | 1.3 | 49.5 | 7.8 |

Example 10

This example describes the production of industrial chemicals via ethenolysis using catalyst 24. Using the general procedure and conditions described in Example 3, the ethenolysis of conjugated methyl linoleate catalyzed by 24 was monitored over time. The percentages (%) of the ethenolysis products in the reaction mixture over time are recorded in Table 8.

TABLE 8

| Time (hr) | 50 | $C_{10}$ | 52 | $C_{12}$ | $C_{14}$ | $C_{18}$ | 48 | Impurities |
|---|---|---|---|---|---|---|---|---|
| 0.0 | 0.0 | 0.0 | 0.0 | 0.0 | 0.0 | 0.0 | 98.4 | 1.6 |
| 0.5 | 0.6 | 1.0 | 2.6 | 1.0 | 1.3 | 6.8 | 51.2 | 35.5 |
| 2.0 | 0.6 | 1.0 | 2.7 | 0.8 | 1.3 | 6.8 | 50.2 | 36.6 |
| 7.0 | 0.9 | 1.0 | 2.5 | 0.6 | 1.4 | 7.0 | 52.2 | 34.4 |
| 17.50 | 0.0 | 1.0 | 2.9 | 0.9 | 1.0 | 6.5 | 50.4 | 37.3 |

Example 11

With the use of a high-pressure Parr reactor, ethenolysis reactions of methyl Δ9,11-octadecenoate (Scheme 6, compound 48) were run at room temperature (24° C.) as in Examples 3-10 except that the ethylene pressure was increased to 800 psi (5517 kPa). Samples were analyzed as previously described. The percentages (%) of the ethenolysis products observed in the reaction mixture at 2 hours with different catalysts are recorded in Table 9.

TABLE 9

| Time (hr) | 50 | $C_{10}$ | 52 | $C_{12}$ | $C_{14}$ | $C_{18}$ | 48 | Impurities |
|---|---|---|---|---|---|---|---|---|
| 601 | 5.4 | 16.6 | 19.3 | 7.1 | 0.0 | 0.0 | 49.1 | 2.5 |
| 823 | 5.9 | 18.4 | 20.9 | 7.9 | 0.0 | 0.0 | 41.1 | 5.8 |
| 712 | 4.8 | 6.6 | 8.2 | 3.6 | 0.1 | 2.8 | 60.2 | 13.8 |
| 933 | 1.2 | 2.1 | 2.6 | 0.7 | 0.2 | 3.0 | 67.9 | 22.5 |

It will be apparent to those skilled in the art that various modifications and variations can be made in the present method without departing from the scope or spirit of the disclosure. Other embodiments of the method will be apparent to those skilled in the art from consideration of the specification and practice of the procedures disclosed herein. It is intended that the specification and examples be considered as exemplary only, with a true scope and spirit of the invention being indicated by the following claims.

We claim:
1. A process for producing an industrial chemical, comprising:
    providing an isomerization precursor;
    isomerizing a site of unsaturation in the precursor to produce an isomerized derivative; and
    reacting the isomerized derivative with an unsaturated compound in the presence of a metathesis catalyst to produce at least one desired industrial chemical, where the isomerization precursor is an unsaturated fatty acid or fatty acid derivative.
2. The process according to claim 1 where the fatty acid or fatty acid derivative is a polyunsaturated fatty acid.
3. The process according to claim 1 where the metathesis catalyst is a ruthenium-based catalyst.
4. The process according to claim 1 where isomerizing the fatty acid or fatty acid derivative includes contacting the fatty acid or fatty acid derivative with an enzyme.
5. The process according to claim 1 where isomerizing produces a conjugated diene derivative.
6. The process according to claim 5 where the conjugated diene derivative is a conjugated linoleic acid.
7. The process according to claim 6 where the conjugated linoleic acids 18:2 Δ9,11 linoleic acid.
8. The process according to claim 1 where reacting the isomerized derivative produces at least one compound selected from the group consisting of butadiene, 1-octene, 9-decenoic acid, derivatives thereof, and combinations thereof.
9. The process according to claim 1 where reacting the fatty acid or fatty acid derivative with an unsaturated compound produces at least one compound selected from the group consisting of butadiene, 1-octene, 9-decenoic acid, derivatives thereof, and combinations thereof.
10. The process according to claim 9 where reacting the fatty acid or fatty acid derivative with an unsaturated compound produces 1-octene.
11. A process for producing l-octene, comprising:
    providing linoleic acid or a derivative thereof;
    enzymatically isomerizing a site of unsaturation in the linoleic acid or derivative thereof to produce an isomerized linoleic acid or isomerized lower ester of linoleic acid; and
    reacting the isomerized linoleic acid or isomerized lower ester of linoleic acid with a metathesis catalyst in the presence of ethylene, thereby producing 1-octene.
12. The process according to claim 11 where the isomerized linoleic acid is Δ9,11-octadecadienoic acid.

13. The process according to claim 12 where Δ9,11-octadecadienoic acid is esterified to provide a lower alkyl ester prior to reacting with ethylene in the presence of a metathesis catalyst.

14. The process according to claim 11 where the metathesis catalyst is a ruthenium-based catalyst.

15. The process according to claim 14 where the metathesis catalyst is

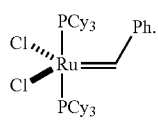

16. The process according to claim 11 where the linoleic acid is derived from soybean oil.

17. A process for producing 1-octene, comprising:
    providing linoleic acid from soybean oil;
    contacting the linoleic acid with a linoleate isomerase to produce Δ9,11-octadecadienoic acid;
    esterifying the Δ9,11-octadecadienoic acid to produce a lower alkyl ester; and
    contacting the ester with a metathesis catalyst in the presence of ethylene, thereby producing 1-octene.

18. The process according to claim 17 where contacting the ester with a metathesis catalyst in the presence of ethylene produces a 9-decenoate ester.

19. The process according to claim 17 where the catalyst is a ruthenium based catalyst.

20. The process according to claim 19 where the catalyst is selected from the group consisting of

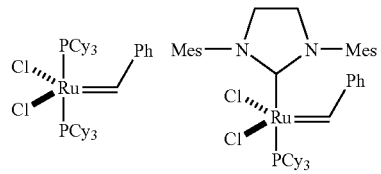

-continued

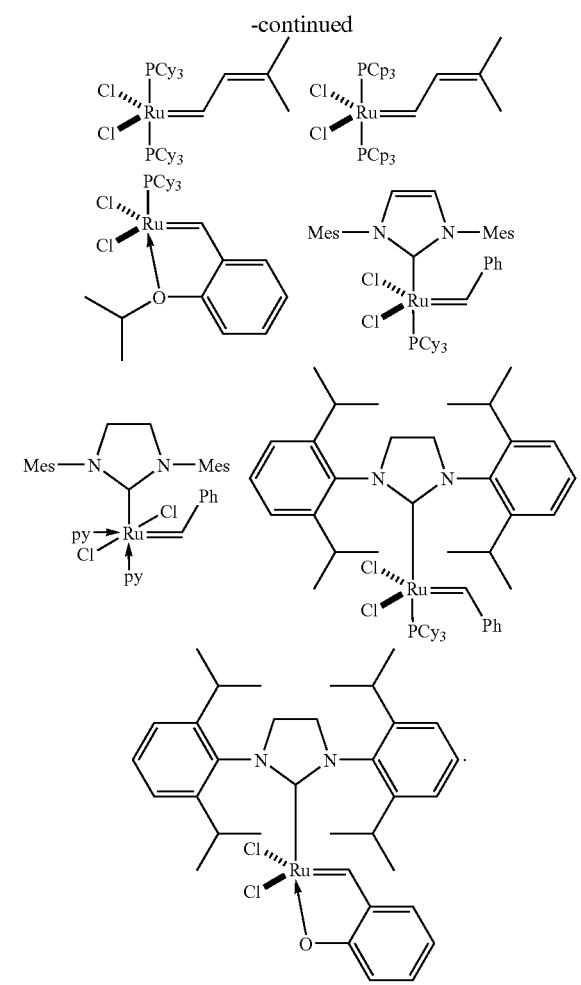

21. A process for producing 1-octene, comprising:
    providing a fatty acid diene or an ester thereof;
    converting the fatty acid diene or the ester thereof to vaccenic acid or an ester thereof;
    contacting the vaccenic acid or an ester thereof with a metathesis catalyst in the presence of ethylene, thereby producing 1-octene.

* * * * *

UNITED STATES PATENT AND TRADEMARK OFFICE
CERTIFICATE OF CORRECTION

| | |
|---|---|
| PATENT NO. | : 7,960,599 B2 |
| APPLICATION NO. | : 10/542167 |
| DATED | : June 14, 2011 |
| INVENTOR(S) | : James R. Millis et al. |

Page 1 of 1

It is certified that error appears in the above-identified patent and that said Letters Patent is hereby corrected as shown below:

In the Claims

In column 20, claim 11, line 61, after "isomerized lower ester" replace "oflinoleic" with --of linoleic--.

Signed and Sealed this
Tenth Day of January, 2012

David J. Kappos
*Director of the United States Patent and Trademark Office*